United States Patent [19]

Eckerle et al.

[11] Patent Number: 5,243,992
[45] Date of Patent: Sep. 14, 1993

[54] PULSE RATE SENSOR SYSTEM

[75] Inventors: Joseph S. Eckerle, Redwood City; Dale W. Ploeger, San Francisco; Steven T. Holmes, Palo Alto; Thomas P. Low, Woodside; Rudolf Elbrecht, Los Altos; Philip R. Jeuck, III, Menlo Park; Ronald E. Pelrine, Menlo Park; Victor T. Newton, Jr., Menlo Park, all of Calif.

[73] Assignee: Colin Electronics Co., Ltd., Aichi, Japan

[21] Appl. No.: 502,028

[22] Filed: Mar. 30, 1990

[51] Int. Cl.⁵ ............................................. A61B 5/02
[52] U.S. Cl. .................................. 128/690; 128/672
[58] Field of Search ............... 128/687, 722, 699, 689, 128/677, 681, 683, 690

[56] References Cited

U.S. PATENT DOCUMENTS

| | | | |
|---|---|---|---|
| 3,999,537 | 12/1976 | Noiles | 128/687 |
| 4,058,118 | 11/1977 | Stupay et al. | 128/2.05 T |
| 4,086,916 | 5/1978 | Freeman et al. | 128/690 |
| 4,181,134 | 1/1980 | Mason et al. | 128/689 |
| 4,202,350 | 5/1980 | Walton | 128/690 |
| 4,239,048 | 12/1980 | Steuer | 128/666 |
| 4,307,728 | 12/1981 | Walton | 128/687 |
| 4,353,372 | 10/1982 | Ayer | 128/640 |
| 4,409,983 | 10/1983 | Albert | 128/690 |
| 4,456,959 | 6/1984 | Hirano et al. | 364/417 |
| 4,646,749 | 3/1987 | Berger et al. | 128/678 |
| 4,667,680 | 5/1987 | Ellis | 128/672 |
| 4,712,179 | 12/1987 | Heimer | 364/417 |
| 4,735,213 | 4/1988 | Shirasaki | 128/681 |
| 4,799,491 | 1/1989 | Eckerle | 128/672 |
| 4,802,488 | 2/1989 | Eckerle | 128/672 |
| 4,836,213 | 6/1989 | Wenzel et al. | 128/672 |

Primary Examiner—Lee S. Cohen
Assistant Examiner—Marianne H. Parker
Attorney, Agent, or Firm—Oliff & Berridge

[57] ABSTRACT

A pulse rate sensor system is packaged in a wristwatch sized assembly and is worn by the user to provide an accurate determination of pulse rate. A tonometer sensor is provided to detect heartbeat pressure waves produced by a superficial artery. A microcomputer manipulates the unprocessed tonometer sensor element signals using multiple algorithms to determine an accurate pulse rate.

36 Claims, 9 Drawing Sheets

| ELEMENT # | RAW SIGNAL | AVERAGED SIGNAL | DIFFERENTIALLY ENHANCED SIGNAL |
|---|---|---|---|
| 1 | 10 | 10 | 0 |
| 2 | -5 | 10 | -15 |
| 3 | 25 | 10 | 15 |

FIG. 6

| ICOR | CORELA(ICOR) (at t-1) | BP | DSUM | NSUM | CORELA(ICOR) (at t) |
|---|---|---|---|---|---|
| 1 | 10 | 20 | 400 | 200 | 20 |
| 2 | -30 | -5 | 425 | 350 | -5 |
| 3 | 50 | 70 | 5325 | 3850 | 70 |

FIG. 7

PULSE RATE SENSOR SYSTEM

FIELD OF THE INVENTION

The present invention relates to pulse monitors with visual readouts of pulse rate and more particularly to a tonometer sensor pulse rate monitor which employs multiple noise and motion artifact rejection methods to determine an accurate pulse rate.

BACKGROUND OF THE INVENTION

The present invention relates generally to a method and apparatus for measuring and displaying pulse rate with increased accuracy. More specifically, the present invention provides a method for increasing the accuracy of a pulse rate sensing system by means of a novel pressure sensing array and multiple methods for identification and elimination of artifacts.

Other methods and apparatus are known for measuring pulse rates and for rejecting pulse artifacts. For example, U.S. Pat. No. 4,409,983 shows a pulse measuring device which employs multiple transducers connected to averaging circuits and differential amplifiers. This invention helps separate signals corresponding to motion artifacts from the signal corresponding to a heartbeat pulse. Other apparatus and methods for removing motion artifacts are disclosed in U.S. Pat. Nos. 4,307,728, 4,202,350, 4,667,680, 4,239,048, 4,181,134 and 4,456,959. Methods used to reduce signal errors include the use of windowing and averaging techniques and auto correlation algorithms.

The pulse rate sensor systems described above are subject to several sources of inaccuracies. First, it is difficult to reject motion and noise artifacts in many of these systems. This is especially true for systems employing a single sensor element. (See U.S. Pat. Nos. 4,202,350 and 4,239,048.) These systems have no physical means for receiving both a pulse-plus-artifact signal and a separate artifact signal. Other means are required to compensate for, or eliminate, the error caused by artifacts such as motion artifacts. Signal processing techniques such as filtering and windowing are often used.

Even those systems or methods which employ multiple sensor elements inaccurately measure pulse rate because only a single method is used for enhanced signal processing. For example, different types of motion artifacts can occur simultaneously, and with other pertubations, on the pulse sensor. It is also not unusual for signal errors to be interpreted as pulses or for actual pulses to be missed by the pulse sensor. Methods of pulse rate determination which do not compensate for these errors are inherently inaccurate under real-world conditions ere artifacts are present.

For example, if a pulse rate system detects a "pulse" caused by noise, several adverse results may be seen. The pulse rate system could use the noise as the basis for windowing the signal. The pulse rate system could simply use this "pulse" as part of the overall pulse rate calculation. In addition, the pulse rate system could recognize the noise as noise and subtract out the noise, in some cases subtracting out a valid signal as well.

Another source of inaccuracy that occurs using pulse measuring devices that measure pressure variations caused by a subject's pulse (see U.S. Pat. No. 4,409,983 for example) is inverted pulse waveforms. An inverted waveform can occur when the housing that holds the pressure sensitive element(s) is located on the artery, but the pressure sensitive element(s) itself is located off the artery. In this case the subject's pulse can push up on the housing and lessen the pressure on the pressure sensitive element. The result is that a pulse waveform is still received, but it is inverted and shows a negative relative pressure. Pulse measuring devices which rely on pressure measurements but can correctly interpret only positive pressure waveforms must be placed and held accurately on the artery, creating additional demands on attachment of the device and/or lowering comfort to the user.

Additionally, pronounced dichrotic notches can be found in the pulse of many people. When dichrotic notches are present there are two rises and two falls in blood pressure during a single heartbeat. These can be mistakenly interpreted as two heartbeats, leading to a major inaccuracy in pulse rate measurement.

The present invention overcomes the problems encountered with other pulse rate sensors by applying the principles of arterial tonometry for signal acquisition for a pulse rate sensor. In the invention, multiple algorithms are used in signal processing and pulse rate calculation to compensate for multiple signal errors which could occur during pulse rate measurement.

The principles of arterial tonometry are described in several U.S. Patents including: U.S. Pat. Nos. 3,219,035; 4,799,491 and 4,802,488. These principles are also described in several publications including an article entitled "Tonometry, Arterial," in Volume 4 of the Encyclopedia of Medical Devices and Instruments. (J. G. Webster, Editor, John Wiley & Sons, 1988). All of these references discuss arterial tonometry as used for the measurement of blood pressure.

For blood pressure measurement, it is desirable to flatten a section of the arterial wall as described in these references. Flattening is produced by exerting an appropriate hold down force on the tonometer sensor. For pulse sensing, significant flattening of the arterial wall is not necessary and a lower hold down force can be used. This results in greater comfort for the wearer.

SUMMARY OF THE INVENTION

Accordingly, the present invention has been developed to overcome the foregoing shortcomings of existing pulse rate sensor systems.

It is therefore an object of the present invention to provide a method and an apparatus for measuring pulse rates using arterial tonometry techniques including a sensor array with multiple sensing elements disposed in an array, in order to provide increased accuracy in the determination of pulse rate.

Another object of the present invention is to increase the accuracy of the displayed pulse rate by calculating the displayed pulse rate using only pulse rates determined to be valid.

A further object of the present invention is to determine whether pulses detected are valid, based on the correlation between the present pulse and the previous pulse.

A still further object of the present invention is to remove motion artifacts from the sensor element signals by subtracting a value from all these signals based on a spatially weighted average of these signals.

An additional object of the present invention is to cancel out artifacts from a sensor element which exceed a level predetermined to be the maximum level of a valid blood pressure signal.

Still another object of the present invention is to accurately process inverted waveforms caused by misalignment or shifting of the sensor elements relative to an underlying artery.

These and other objects and advantages are achieved in accordance with the present invention by the steps of: sensing at least one blood pressure waveform signal at a predetermined sampling period using a tonometer sensor having a plurality of sensor elements disposed in an array; producing a plurality of sensor element signals, at least one of the sensor element signals corresponding to the at least one blood pressure signal; correcting the sensor element signals using a correction factor based on one characteristic of the sensor element signals; calculating a plurality of slopes based on the corrected sensor element signals; selecting a corrected sensor element signal corresponding to one of the sensor elements, the selected sensor element signal having slopes greater than a predetermined slope threshold; determining a plurality of pulse rates based on the selected sensor element signal; computing a value corresponding to the autocorrelation of the corrected sensor element signal over a predetermined time period; and calculating a display pulse rate based on at least two of the pulse rates, each of the two pulse rates having the value within a predetermined range.

These and other objects and advantages are achieved in accordance with the preferred embodiment of the present invention comprising: a tonometer sensor means having a plurality of pressure sensing elements disposed in an array, for sensing a blood pressure waveform on at least one of the pressure sensing elements and producing a plurality of sensor element signals, at least one of the sensor element signals being indicative of the blood pressure acting on at least one of the pressure sensing elements; means for pivoting the tonometer sensor means about a pair of axes; means for pressing the tonometer sensor means against a radial artery of a subject; means for anchoring the pressing means on a dorsal side of the subject; central processing means for determining a pulse rate based on at least one of the sensor element signals received from the tonometer sensor means; means for displaying the pulse rate; and means for holding the anchoring means on the subject, the holding means at no time contacting the pressing means.

BRIEF DESCRIPTION OF THE DRAWINGS

The preferred embodiments are described with reference to the drawings in which:

FIG. 6 is a table illustrating the effect of differential enhancement on raw sensor element signal levels;

FIG. 7 is a table illustrating the calculations of the correlation algorithm.

DESCRIPTION OF THE PREFERRED EMBODIMENTS

Figure 1:
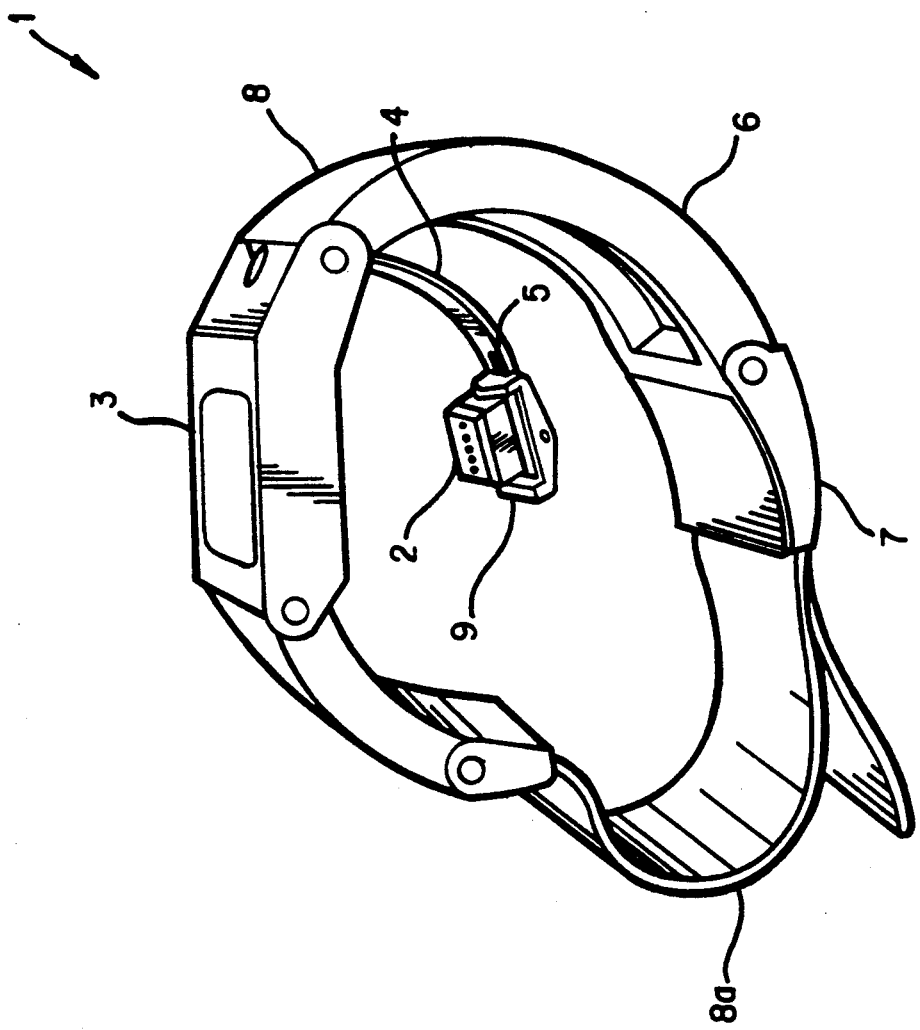
FIG. 1 is a general arrangement of a pulse rate sensor system illustrating a pulse rate sensor connected to a case assembly.

Referring to FIG. 1, a pulse rate monitor 1 in accordance with the preferred embodiment of the present invention is shown having a tonometer sensor 2 and a case 3 housing processing and display circuitry. The tonometer sensor 2 is mounted in a gimbal assembly 9 which in turn is connected to case 3 by a spring 4. Spring 4 includes a sensor position adjustment 5 section at the connection point between gimbal assembly 9 and spring 4.

Figure 2:
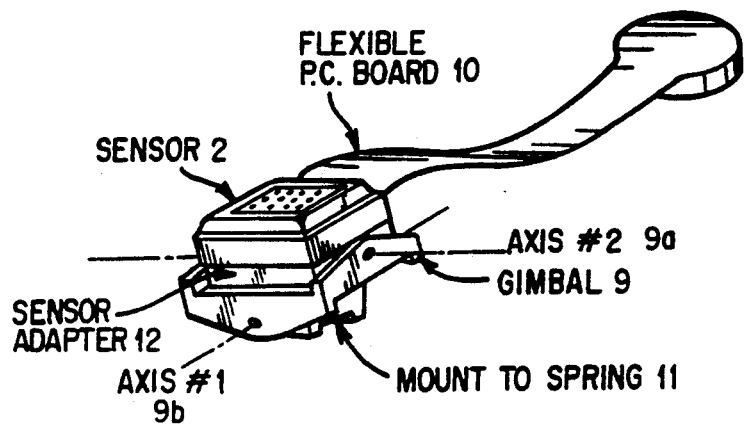
FIG. 2 is a perspective view of the tonometer sensor supported in a gimbal assembly.

Further details of this arrangement are shown in FIG. 2, which uses the same component designations found in FIG. 1, where possible. The tonometer sensor 2 is attached to a sensor adapter 12 which, in turn is pinned to the gimbal assembly 9 at axis number 2. A spring mounting pad 11 is pinned along axis number 1 of gimbal assembly 9, mounting pad 11 being the point at which sensor position adjustment 5 connects to gimbal assembly 9. Flexible printed circuit 10 connects the tonometer sensor 2 to circuitry (shown in FIG. 4) in case 3.

Tonometer sensor 2 is an array of pressure or force sensitive elements fabricated into a single structure. Standard photolithographic manufacturing techniques can be used to construct the tonometer sensor. Experimental testing indicates that about 3 to 6 individual sensor elements are necessary for good accuracy in pulse rate measurement but even a single sensor element adapted for use with the method and apparatus of the present invention will produce more accurate pulse rate determinations.

Referring again to FIG. 1., the remainder of the pulse rate monitor 1 will be described in terms of wearing the pulse rate monitor 1. In the preferred embodiment, the pulse rate monitor is worn on the operator's wrist like a wrist watch. When the wearer dons the pulse rate monitor 1, the tonometer sensor 2 is positioned above a radial artery and the case 3 is positioned on the opposite side of the wrist. The case 3, which anchors one end of spring 4, is held in place by strap 8 by cinching an flexible portion 8a of a strap 8 and locking the strap in position by means of a buckle 7. Strap 8 is prevented from directly contacting the tonometer sensor 2, the gimbal assembly 9 and the spring 4 by a protective band 6 which is part of the strap 8. Protective band 6 has a box shaped cutout section which allows it to fit around the tonometer sensor 2, the gimbal assembly 9 and the spring 4, without contacting any of these elements.

The tonometer sensor 2 is held against the artery with a thin cantilever spring 4 which is attached to the case 3. The spring reaches around the wrist to position the tonometer sensor 2. A low profile gimbal assembly 9 (See FIGS. 1 and 2) connects the tonometer sensor 2 to the spring 4 and allows the tonometer sensor 2 to pivot so as to lie flat against the wrist while being worn. Gimbal assembly 9 allows about 20 degrees of rotation about each of its two axes. The position on spring 4 of the tonometer sensor-gimbal assembly 2, 9 is adjustable by means of the sensor position adjustment 5 section of spring 4.

Sensor hold down force must be controlled to provide enough pressure to partially flatten the radial artery but not enough pressure to cause discomfort to the wearer. The optimum hold down force is unique to each individual but ranges from about 100 grams to about 500 grams. Some wearers may require a higher hold down force to obtain a reliable pulse signal from the tonometer sensor 2. Other wearers may be sensitive to the hold down force of the tonometer sensor 2 against their wrists and desire the lowest possible hold down force.

Figures 3A, 3B, 3C:
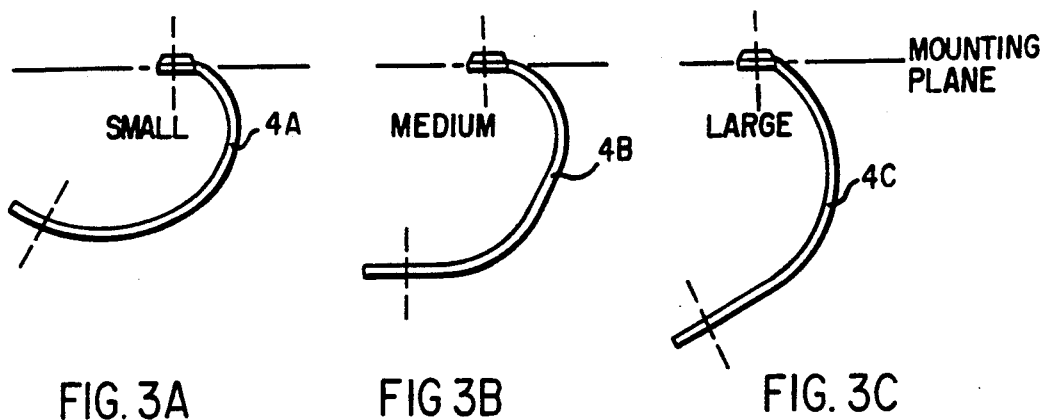
FIGS. 3A, B and C show low, medium and high curvature spring profiles, respectively.

Ideally, since the hold down force of the tonometer sensor 2 is controlled only by the deflection of the spring 4 and since the size and shape of the wrist can vary greatly between individuals, each spring 4 would have to be custom fit for each wearer. In general, three configurations for spring 4, shown in FIGS. 3A, B and C, will suffice to cover the majority of the population. Springs 4A, B and C, shown in FIGS. 3A, B and C, provide adequate length and curvature adjustment to cover the general population. The springs 4A, 4B and 4C differ only in their radius of curvature.

Figure 8A:
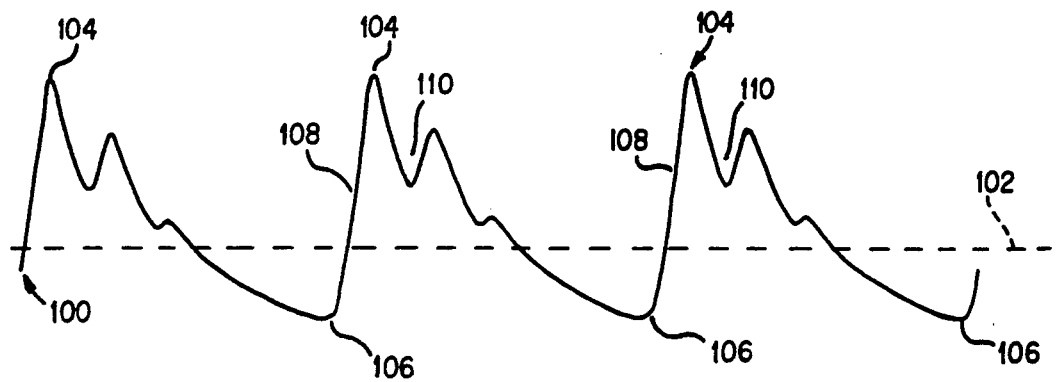
FIGS. 8A and B are graphical representations of normal and inverted blood pressure waveforms, respectively.
Figure 8B:
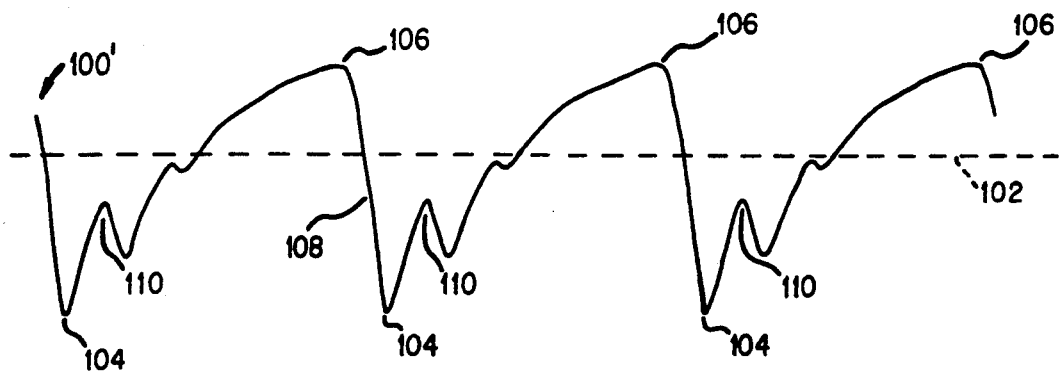

The discussion below of the computation of the pulse rate can best be understood by first understanding the important features of a normal blood pressure waveform. Referring to FIG. 8A a normal blood pressure waveform 100 with an average blood pressure 102 is shown. The point 104 on the waveform 100 where blood pressure is maximum is referred to as systole, while the point 106 where blood pressure is a minimum is referred to as diastole. It is known from scientific studies that the maximum absolute value of the slope of wave form 100 occurs just prior to systole, in region 108, when the blood pressure is rising from diastole. A dichrotic notch 110 is present in the blood pressure waveform 100 of some subjects. Referring to FIG. 8B, an inverted waveform 100' is shown having systole (104), diastole (106), the region (108) and dichrotic notch (110).

Figure 4:
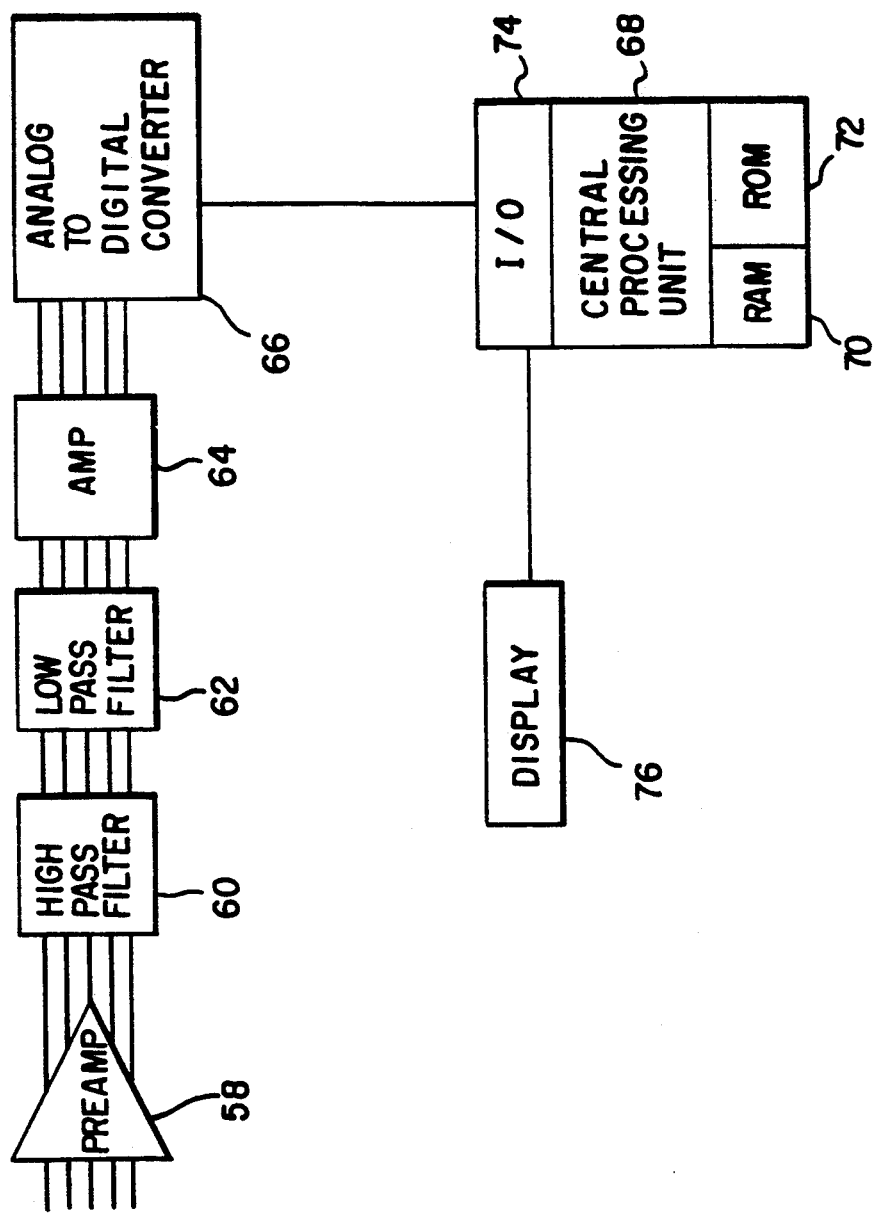
FIG. 4 is a block diagram of the pulse rate processing circuitry in accordance with the preferred embodiment of the present invention.
Figure 5A:
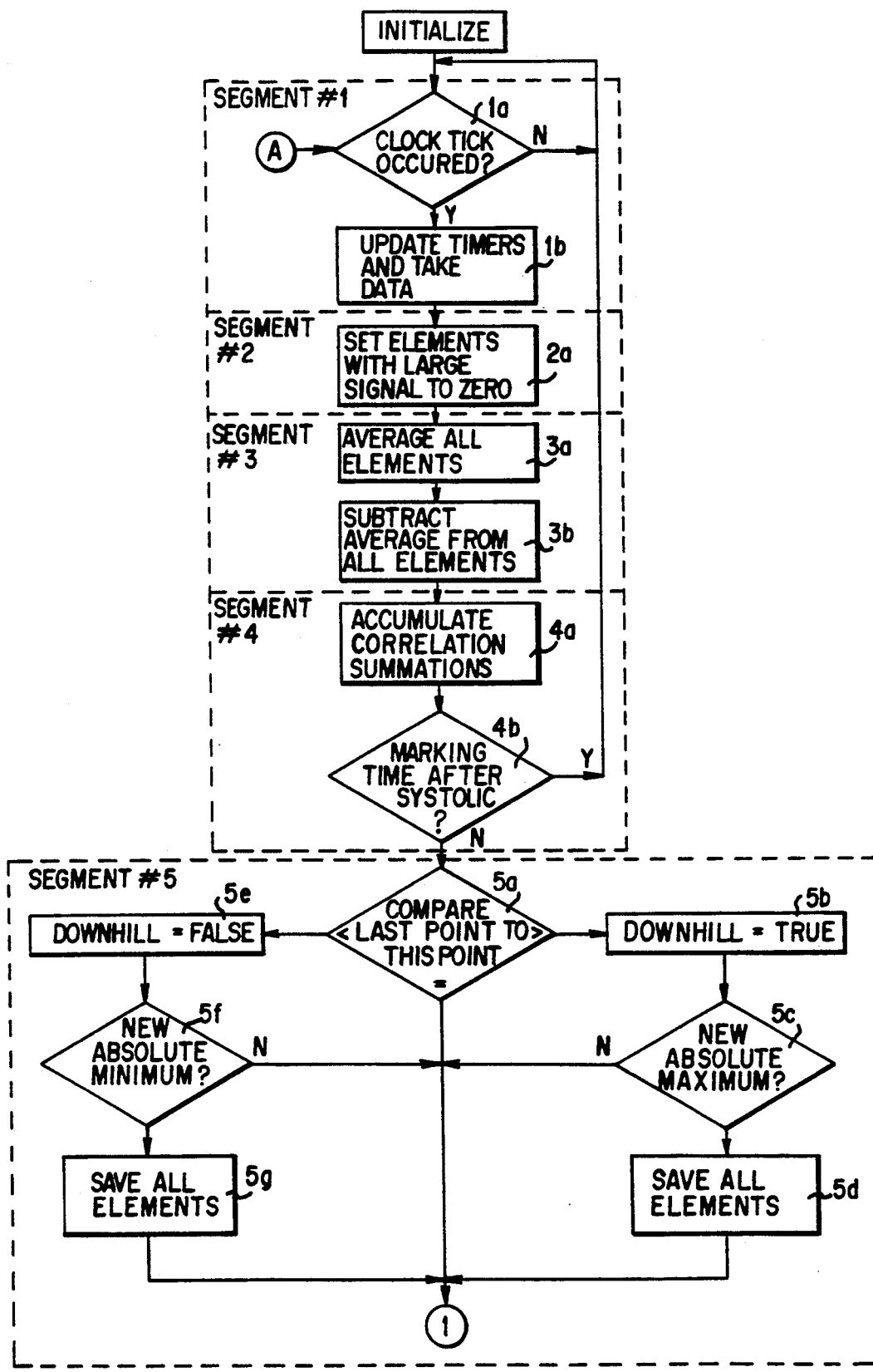
FIGS. 5A, B, C and D are a flowchart describing a pulse rate measurement and compensation method in accordance with one embodiment of the present invention.
Figure 5B:
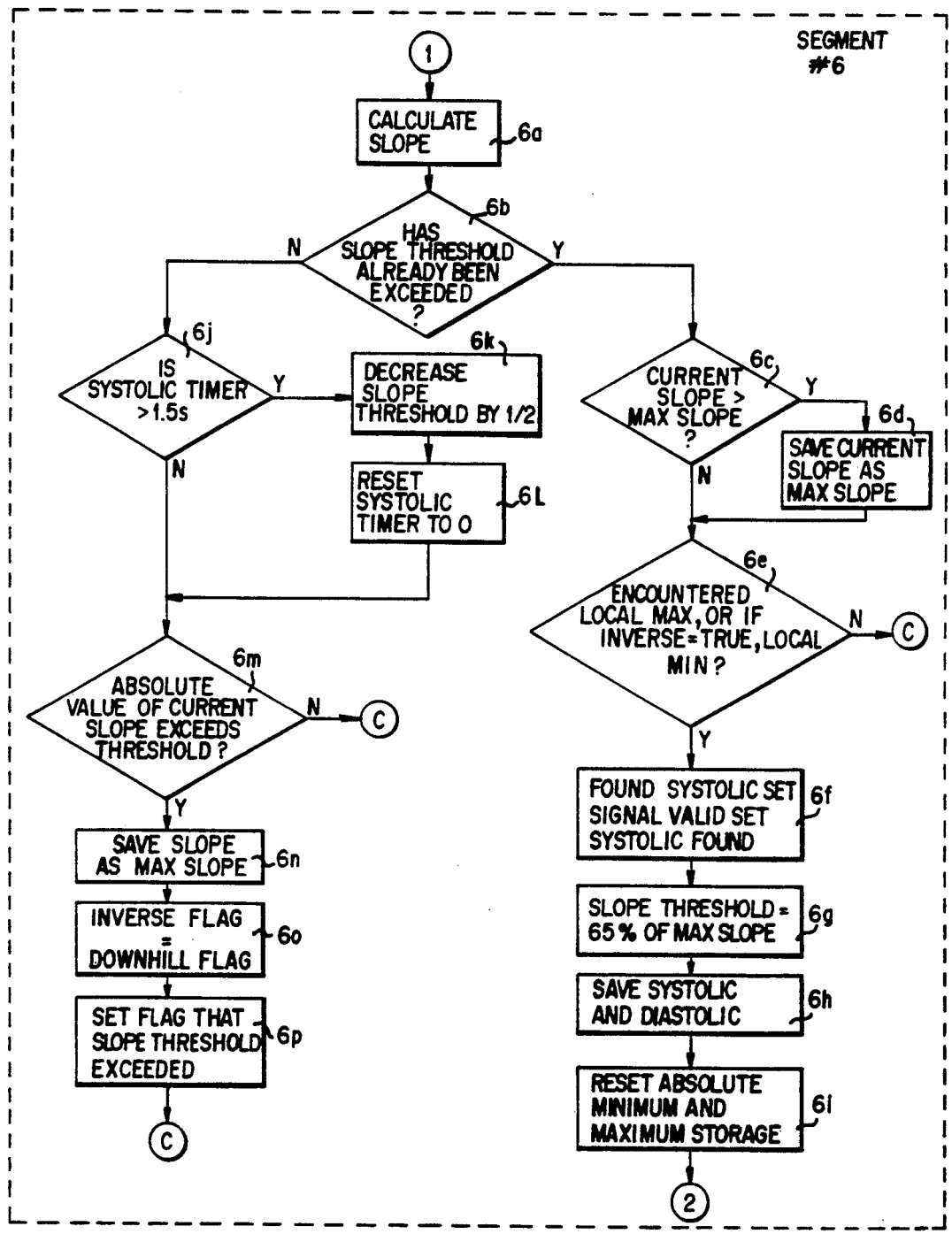
Figure 5C:
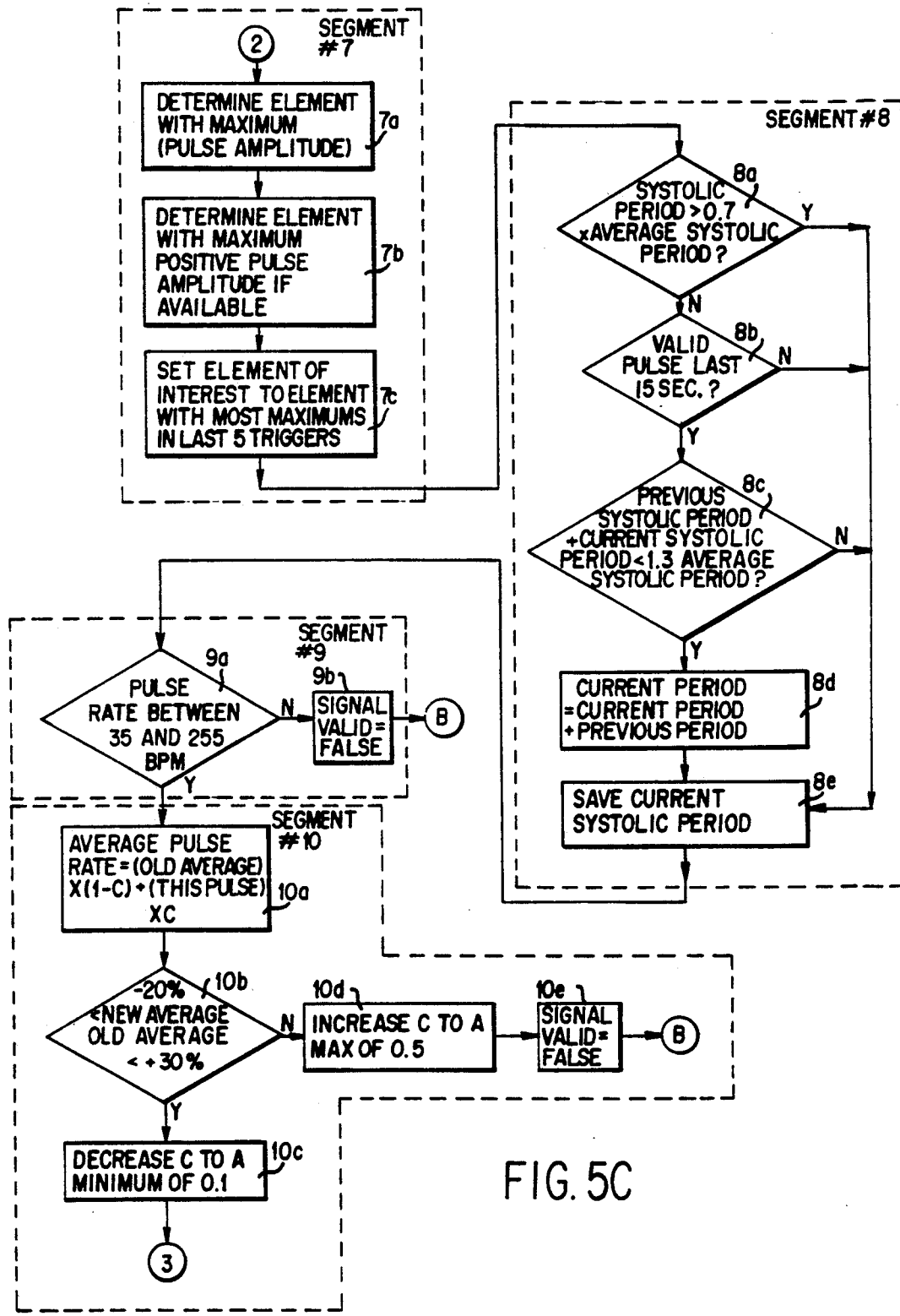

Computation of pulse rate is performed by electronic circuitry shown in FIG. 4 and located in case 3, in accordance with the flow chart shown in FIGS. 5A, B, C and D.

Referring first to FIG. 4, circuitry to process tonometer signals and compute pulse rate in accordance with the present invention comprises: a preamplifier 58; a high pass filter 60; a low pass filter 62; an amplifier 64; an analog-to-digital digital converter (ADC) 66; a central processing unit (CPU) 68; random access memory (RAM) 70; read only memory (ROM) 72; input/output unit (I/O) 74 and display 76. As shown in FIG. 4, the preamplifier 58, filters 60 and 62, amplifier 64 and ADC 66 each include inputs corresponding to the individual sensor elements.

During operation, the output of all sensor elements of tonometer sensor 2 are routed to preamplifier 58 which amplifies the signals before filtering. The output of preamplifier 58 is the input to high pass filter 60 which removes the DC and very low frequency components of the signals. The output of the high pass filter 60 is the input to the low pass filter 62 which removes some of the high frequency components of the signal. (High pass filter 60 coupled with low pass filter 62 effectively act as a band pass filter.) The preferred bandwidth of the effective band pass filer is about 0.1–30 Hz. After filtering, the signals are amplified by amplifier 64 to a level compatible with the ADC 66. ADC 66 multiplexes the signals and converts them to digital data which is sent to I/O 74. CPU 68 reads the digital data form I/O 74 and stores the digital data in RAM 70.

RAM 70 is segmented to form a plurality of data buffers for storage of digital data representing sensor element signals, counts, flag settings and calculated values. A ROM 72 contains the operating program software for CPU 68. CPU 68, through I/O 74, receives digital data from ADC 66 and outputs pulse rate calculations to display 76.

The operation of CPU 68 is best understood by referring to the flow chart of FIGS. 5A, B, C and D.

When the pulse rate sensor system is turned on or reset by the wearer, the system goes through an initialization routine to clear stored data. At this point, a clock (not shown) starts and a clock signal is provided to the CPU 68 to set a predetermined sampling period.

Referring to FIG. 5A, while performing segment 1 of the program, sub-step 1a checks to see if a clock tick has occurred. If a clock tick is not detected at sub-step 1a, the cycle repeats. If a clock tick is detected, the CPU 68 executes sub-step 1b and samples the outputs of all sensor elements of the tonometer sensor 2. In addition, system timers are updated. Control then passes to program segment 2.

During program segment 2, each data element for each sensor element is checked to see if it exceeds a predetermined maximum value. If an actual value exceeds the predetermined maximum value, i.e. the predetermined maximum amplitude, the data from that sensor element is set to zero. The program also sets a flag so that all data from that sensor element is set to zero for the next five seconds. This eliminates unusually large signals which are usually noise. Program control then passes to program segment 3.

Differential enhancement of the signal occurs during execution of program segment 3. During sub-step 3a, all signals from sensor elements not previously set to zero are averaged to produce a spatially weighted average signal. In the preferred embodiment, the weighted factor is about 1.0, but can be adjusted as described below. At sub-step 3b, the spatially weighted average signal is subtracted from each of the actual sensor element signals.

The differential enhancement algorithm reduces motion artifacts in the tonometer sensor signals. This algorithm can only be used when multiple sensor elements are employed simultaneously. Since all of the sensor element signals are often affected equally by a motion artifact, the differential enhancement algorithm aids in distinguishing between artifacts and blood pressure signals. For example, motion artifacts such as footsteps usually affect all sensor elements in the same way. Blood pressure signals, on the other hand, affect only sensor elements which are directly over or very near to the artery.

Differential enhancement adds all of the signals from all of the sensor elements together and forms a spatially weighted average signal. If each sensor element is affected in the same way by a motion, the spatially weighted average signal will be an accurate representation of the motion artifact. This spatially weighted average signal is then subtracted from each individual sensor element signal to form a differentially enhanced signal for each sensor element signal. (I.e. an approximation of the motion artifact is subtracted from the raw sensor element signals to produce corrected sensor element signals.) The raw sensor element signals are expected to be either motion artifact signals or motion artifact signals plus blood pressure signals. For example, FIG. 6 shows the effect of the differential enhancement algorithm on the signals from a three element sensor array. Signals for only one clock tick are shown.

Differential enhancement is part of a larger class of algorithms where the processed output for each value is a weighted sum of the unprocessed values. For example, differential enhancement of three raw values produces a processed output for value 1 as follows:

Processed Value 1 = (2/3)(raw value 1) +
(−1/3)(raw value 2) + (−1/3)(raw value 3).

Other extensions of this procedure are possible and different weighting factors than those used by the basic differential enhancement algorithm are possible without departing from the teachings of this disclosure. For example, it may be advantageous to assign large negative weights to sensor element signals far from a selected sensor element and large positive weights to sensor element signals located near to a selected sensor element.

Returning to FIG. 5A, after performing program segment 3, program control passes to program segment 4 where the differentially enhanced signal data is processed by a correlation algorithm.

The correlation algorithm computes a quantitative measure of the similarity between sensor waveforms over a predetermined time period of about two consecutive heartbeats. In principle, the shape of a person's blood pressure waveform will be fairly constant from one heartbeat to the next. The correlation algorithm compares the blood pressure waveform for the current heartbeat with a previously recorded waveform for the preceding heartbeat.

The processor executes the correlation algorithm as follows. A variable, ICOR, is used as a counter to keep track of the number of clock "ticks" (i.e. the elapsed time) that the processor has spent looking for a systole. At the start, ICOR is set equal to 1. ICOR is then incremented by one for each subsequent clock tick (i.e. each time data is sampled from the sensor) When ICOR is set equal to 1, the variables DSUM and NSUM, described below, are both set equal to zero. The data from the selected element of the tonometer sensor between the time when the processor starts looking for a systole and the time when it actually finds a (presumed valid) systole is stored in an array, called CORELA. ICOR is used as a pointer for the array CORELA, i.e. the value of the data from the selected element after ICOR clock ticks have occurred (after the start of looking for a systole) is stored in CORELA(ICOR).

For example, suppose a similar procedure had been used for the previous heartbeat, and the values from the selected element had been stored in another array, CORELB. After the systole is found for the present heartbeat, the correlation coefficient, COR, may be calculated. The correlation coefficient between the pressure waveforms for the current and previous heartbeats is mathematically defined as:

$$COR = \sum_j \frac{(CORELA(j) \cdot CORELB(j))}{(CORELA(j) \cdot CORELA(j))} \quad (1)$$

where the summation, , is over all values of elapsed time, j, from the start of looking for the systole. If the current heartbeat is exactly identical to the previous heartbeat, the array, CORELB, will be equal to the array, CORELA, and the correlation coefficient, COR, will be equal to 1. If COR differs greatly from 1, the two waveforms are not similar and at least one of them is probably distorted by a movement artifact. The program accepts values of COR between about 0.6 and 2.0 as valid pulses, but rejects or ignores pulses that have correlation coefficients outside this predetermined range. Of course, different acceptance ranges for COR may be used without departing from the teachings of this disclosure.

The traditional mathematical definition of the correlation coefficient applies only when the two waveforms being correlated (CORELA and CORELB of the above example) have exactly the same duration. In other words, Eq. (1) is mathematically rigorous only when both heartbeats' durations are equal. The present invention departs from this mathematical constraint and allows COR to be computed even if the durations of the two heartbeats are not exactly equal. Eq. (1) can be used to advantage in the case where the two waveforms do not have equal duration since Eq. (1) can be used very effectively to recognize movement artifacts even though it is not used in a mathematically rigorous way.

In the preferred embodiment, the array, CORELB, of the above illustration is not used. Instead, a running summation of the numerator of Eq. (1), called NSUM, and of the denominator of Eq. (1), called DSUM, are updated after each sample of sensor data is obtained. Specifically, if BP(ELEMENT) is the pressure measured by a selected element at time ICOR, the following sequence is executed:

10 $DSUM = DSUM + (BP(ELEMENT) \times BP(ELEMENT))$

20 $NSUM = NSUM + BP(ELEMENT) \times CORELA(ICOR)$

30 $CORELA(ICOR) = BP(ELEMENT)$

The correlation coefficient is then simply calculated after systole is found as COR=NSUM/DSUM. This procedure works because in line 20 of the above code CORELA(ICOR) still contains the pressure data from the previous heartbeat. Line 30 updates CORELA for the calculation on the next (future) heartbeat. Use of this running summation (in place of the two arrays, CORELA and CORELB, of Eq. (1)) is advantageous because it reduces computer speed and memory requirements. However, Eq. (1) defines the correlation coefficient so it may be calculated by other procedures without departing from the teachings of this disclosure.

The table shown in FIG. 7 gives an example of what the relevant variables hold for a few samples of hypothetical data. If systole occurred at ICOR=3 (in reality the waveform normally extends for many more samples before a systole is found) the correlation coefficient would be calculated as $COR = NSUM/DSUM = 3850/5325 = 0.723$ L Feed and this heartbeat would be accepted as valid by the acceptance criterion described above.

Finally, the correlation coefficient in other applications is sometimes also defined as:

$COR = (CORELA(j) \cdot CORELB(j))/(AMPA)x(AMPB)$ where AMPA=sqrt(DSUM), AMPB=sqrt(DSUM'), and DSUM' is the value of DSUM for the previous heartbeat. This definition makes the correlation coefficient independent of any overall gain change between one heartbeat and the next.

After executing sub-step 4a, the program checks to see if a systolic peak has been detected within a predetermined number of sampling periods, e.g., the last 0.25 seconds, at sub-step 4b. If the answer is yes, program segment 4 loops back to program segment 1 to accumulate sensor element signals. If the answer is no, program control passes to program segment 5.

A normal, non-inverted pulse waveform will have a fairly large negative slope as the blood pressure drops from its peak value at systole. There can also be a pronounced dichrotic notch which has a local minimum pressure. See FIG. 8A. These features can be mistakenly interpreted by the program as an inverted waveform (i.e. a waveform containing a large negative slope followed by a local minimum). Similar problems can occur with a true inverted waveform, with the dichrotic notch just after systole being mistakenly interpreted as a new, non-inverted pulse. See FIG. 8B. Since the program must be able to correctly handle both normal and inverted waveforms, the best strategy is to turn off normal processing for a short period of time after systolic pressure has been identified. This presents problems for the correlation algorithm, which works best when it has full waveforms to process. The compromise solution is to only collect data and perform correlation processing during the post systolic delay calculated in substep 13b before passing control to program segment 5.

After executing program segment 4, control passes to program segment 5 which accumulates minimum and maximum sensor element signal data. As shown in FIG. 5A, at sub step 5a the current data is compared to the previous data to determine if a selected signal is increasing, decreasing or constant over the time interval of the clock tick. Substep 5e sets the DOWNHILL flag=-False if the signal is increasing while sub-step 5b sets DOWNHILL flag=True if the signal is decreasing. Increasing signals are processed by sub-steps 5e, 5f and 5g while decreasing signals are processed by sub-steps 5b, 5c and 5d. Control then passes to program segment 6.

At sub-step 6a, the processor calculates the slope of the selected sensor element signal. At sub-step 6b, it checks to see if the slope has already exceeded a predetermined slope threshold since the last systole was found (whether valid or invalid). If the slope threshold has already been exceeded since the last systole, processing proceeds according to sub-steps 6c–6i which look for the maximum absolute value of the slope and for the next systole. Systole is assumed to occur at the temporal local maximum for normal waveforms and at the local minimum for inverted waveforms. If a local maximum or local minimum is not encountered, the program steps to program segment 13 which then loops back to program segment 1. A value equal to 65% of the maximum absolute value of the slope is stored and used as the slope threshold value for the next pulse. If the slope threshold has not already been exceeded since the last systole, processing proceeds according to sub-steps 6j–6p to determine if the slope of the signal during the current sampling period exceeds the slope threshold. Sub-step 6m tests whether the absolute value of the current slope exceeds the slope threshold, and if it does exceed the threshold sub-step 6o sets a flag which marks the waveform as normal (threshold exceeded by a positive slope) or inverted (threshold exceeded by a negative slope). Sub-step 6p then steps to program segment 13 which loops back to program segment 1 for additional data acquisition.

Next, once systole has been found (whether valid or invalid), processing continues to program segment 7 to identify the sensor element with the maximum pulse amplitude. The pulse amplitude is measured by the difference between the maximum and minimum signals from a sensor element that have occurred during the current pulse period. At sub-step 7a, all sensor element signals are examined to identify the sensor elements with maximum amplitudes. At sub-step 7b, these signals are examined to identify the sensor element with the maximum positive amplitude. Sub-step 7c selects the actual element of interest as that element which produced the most maximums during the last 5 heartbeats by storing the index value for this signal. Program control then passes to program segment 8.

During program segment 8, the program tests for two triggers during one heartbeat. Sub-step 8a first tests to see if the systolic period, the time between the current and the previous systoles, is within 30 percent of the expected systolic period. If it is, the program jumps to sub-step 8e and stores the current systolic period in RAM 70. If it is not, the program steps to sub-step 8b and tests for a valid pulse in the last 15 seconds. If there has been no valid pulse, the program again steps to sub-step 8e. If a valid pulse has occurred within the last 15 seconds, the program steps to sub-step 8c and executes a 2-Trigger algorithm.

The 2-Trigger algorithm is designed to handle a false slope threshold "trigger" that occurs between 2 valid slope threshold triggers. The name comes from the fact that two threshold triggers are associated with one heartbeat rather than the usual single trigger.

The 2-Trigger algorithm works by comparing the current systolic period, the time between the last two systoles (in the program this variable is called SYSTIM) to a predetermined expected range centered around the expected systolic period, based on the weighted average pulse rate. The 2-Trigger algorithm keeps track of both the current systolic period (whether valid or invalid) and the previous systolic period (whether valid or invalid). In the program this variable is called SYS1.

Referring to program segment 8, if the current systolic period is greater than 70% of the systolic period, nothing is changed and processing continues as if this algorithm did not exist. If this 70% criterion is not met, the processor then determines if there has been a valid pulse during the preceding 15 seconds. If not, processing continues as if the 2-Trigger algorithm did not exist.

In the case where a valid pulse has occurred recently, the processor then compares the sum of the current systolic period and the preceding systolic period. If this sum is less than 130% of the expected systolic period, then SYSTIM is replaced by SYSTIM+SYS1.

In this way, if a noise spike or movement artifact splits the actual systolic period into two parts (previous period plus current period) the processor can correct for this situation. For the next (future) heartbeat the modified SYSTIM will become the previous systolic period, so in principle the 2-Trigger algorithm can handle 3 or more triggers per heartbeat.

The 2-Trigger algorithm affects only the weighted average pulse rate and not the correlation algorithm discussed above. In another preferred embodiment of the present invention, the 2-Trigger algorithm may be adapted to work harmoniously with the correlation algorithm by making the following provisions:

1. ICOR would not be reset if a threshold trigger occurs in an abnormally short time as determined by the weighted average pulse rate.

2. The program would delay looking for a slope threshold trigger after a systole is found to prevent false triggers on the upward slope of the dichrotic notch, as before. During the delay, the correlation processing would continue, i.e. CORELA, NSUM, DSUM, and ICOR would be updated with each clock tick.

The key to making the 2-Trigger algorithm work is to restrict its use. In particular, the 2-Trigger algorithm is not used when more than 15 seconds have elapsed since finding a valid pulse. Also, the algorithm is not used at the start of the program. Once the processor has found a valid pulse, the 2-Trigger algorithm will help to track that pulse. By shutting off the 2-Trigger algorithm when more than 15 seconds have elapsed since finding a valid pulse, the program is prevented from "creating" a pulse that is not really there. The weighted average pulse rate will tend to drift during periods of high noise and large movement artifacts. For long periods of invalid pulses, e.g. greater than 15 seconds, it may drift close to half of the actual pulse rate. If the 2-Trigger algorithm were still active at these times, it could cause the program to lock onto one half of the true pulse rate. In principle, there should also be ½-Trigger (and ⅓-Trigger etc.) algorithms. These would be algorithms that correct for missed slope threshold triggers.

The program then steps to program segment 9. During program segment 9, the program checks to see if the systolic period is within predetermined physiological limits equivalent to about 35 to 255 beats per minute (BPM). If the systolic period is not within these limits, the program steps to program segment 14 and checks to see if a valid pulse has been detected within the last 30 seconds at sub-step 14a. If a valid pulse has been detected, the program steps to program segment 13 which loops back to program segment 1. If a valid pulse has not been detected, sub-step 14b blanks display 76, then steps to program segment 13 which again loops back to program segment 1. If the systolic period is within the predetermined physiological limits, the processor steps to program segment 10.

During program segment 10, the program computes a weighted average pulse rate and then checks to see if the new weighted average pulse rate is within predetermined limits.

At sub step 10a, the weighted average pulse rate is computed as:

$$APR_t = APR_{t-1} \times (1-C) + (PR_t) \times C$$

where:
$APR_t$ = new Average Pulse Rate;
$APR_{t-1}$ = previous Average Pulse Rate;
$PR_t$ = current Pulse Rate; and
C = current weight factor within a predetermined C range and calculated during previous passes through program segment 10.

At sub-step 10b, the program checks to see if the new weighted average pulse rate falls within a predetermined range of about 0.8P to 1.3P, where P is the previous weighted average pulse rate. If the new weighted average pulse rate is within this range the program branches to sub-step 10c, decreases C by a fixed percentage (but not to less than 0.1), stores the new value of C and steps to program segment 11. If the new weighted average pulse rate is outside the 0.8P to 1.3P range, the program executes sub-step 10b which increases the value of C and stores the result. The program then sets an artifact flag at sub-step 10c and steps to program segment 14 for processing as described above.

Figure 5D:
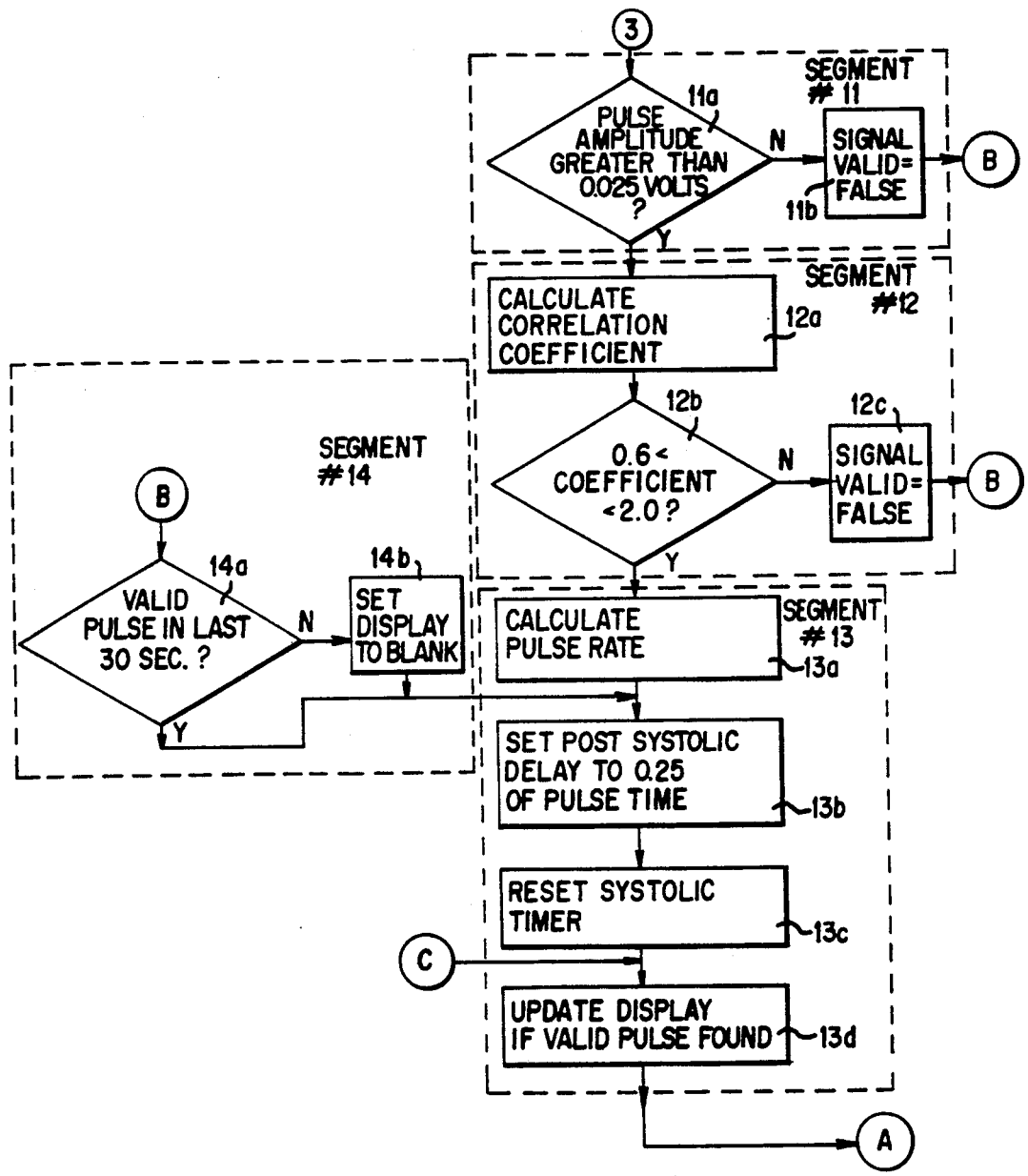

Referring to FIG. 5D, the program segment 11 then checks to see if the pulse amplitude is greater than a predetermined value acting as a noise threshold. This predetermined noise threshold is set to a voltage level corresponding to about a 0.7 mm Hg signal from a sensor element. If the received signal is less than this predetermined noise threshold, an artifact flag is set at sub-step 11b and the program steps to program segment 14. If the pulse amplitude is greater than the predetermined noise threshold, control passes to program segment 12.

During program segment 12, sub-step 12a, the processor computes the correlation coefficient using the equation $$COR = \frac{NSUM}{DSUM}$$

where NSUM and DSUM are the values computed in program segment 4.

At sub-step 12b the program tests to determine if COR is within a predetermined range of values of about $0.6 < COR < 2.0$. If COR is not within this predetermined range of values the artifact flag is set at a sub-step 12c and the program steps to program segment 14. If COR is within the predetermined range, the program branches to program segment 13.

During program segment 13, the pulse rate is calculated and displayed. Sub-step 13a calculates the display pulse rate, which is a weighted average of pulse rates of valid pulses. Unlike the weighted average pulse rate calculated in program segment 10, the display pulse rate is updated only when a valid pulse has been found. Once a valid pulse has been found, the display pulse rate is calculated as:

$$DPR_t = (1-D) \times (DPR_{t-1}) + (D) \times (PR_t)$$

where:
$DPR_6$ = new display pulse rate;
$DPR_{6-1}$ = previous display pulse rate;
$PR_t$ = current pulse rate; and
D = a constant.

In the preferred embodiment, the constant D is a predetermined value of about 0.2.

Program segment 13 then sets the post systolic delay to 0.25 times the pulse period at sub-step 13b and resets the systolic timer at sub-step 13c. At sub-step 13d, the display is updated.

The program then steps to program segment 1 and repeats the pulse rate determination program.

Other embodiments of the disclosed invention are also possible and will be readily apparent to those of ordinary skill in the art. For example, while the apparatus described above is directed towards a pulse rate sensor system, the mechanical components shown in FIGS. 1-4 can be advantageously applied to the determination of a variety of cardiopulmonary parameters, e.g., blood pressure and respiration rate. Since the pulse rate system described above provides features to eliminate or compensate for motion and noise artifacts symptomatic of other sensor systems, the pulse rate system provides identical improvements for sensor systems based on sensing a blood pressure or blood pressure waveform. Based on the pulse rate sensor system described, a family of cardiopulmonary parameter sensor systems can be produced principly by changing the programming logic stored in ROM 72.

Additional improvements to the pulse rate sensor system will be obvious to those of ordinary skill in the art. Program alterations can be used to supplement or replace the program segments described in relation to FIG. 5. For example, the 2-Trigger algorithm can be readily augmented by ½ and ⅓-Trigger algorithms as described above.

Other embodiments of the claimed invention are available by replacing the constant C of program segment 10 with other values. For example, several algorithms can be used to determine the weight, C, in the weighted average pulse rate in different ways. The above-described algorithms and all variations described below, limit C to a predetermined range (a C range) of values between about 10% and 50% (i.e. the current pulse rate is averaged with the weighted average pulse rate, the current pulse rate being given a weight limited to between about 10% and 50%). For example, one variation sets C=k/Rate. This variation makes C inversely proportional to heart rate. The constant of proportionality, k, is chosen so that C=50% when the pulse rate is 60 beats per minute. In another variation, C is given by C=f (Belief). This algorithm sets C=45% when the current pulse rate is within a window centered around the weighted average pulse rate and sets C=15% when the current pulse rate is outside this window. Another way to describe this algorithm is that C is set large when the belief is high that the current pulse rate is correct, and small when the belief is low. In a preferred embodiment, the window chosen is between about 20% below and 30% above the weighted average pulse rate. In yet another variation, C is given by C=k X (DISTIM). This algorithm sets C proportional to the elapsed time, DISTIM, since a valid pulse had been found. The proportionality constant, k, is chosen such that 15 seconds after the last valid pulse had been found, C is equal to about 50%

Those skilled in the art will immediately recognize that additional features of the claimed invention are possible to increase the inventions usefulness in cardiovascular fitness applications. For example, cardiovascular fitness is obtained by raising the pulse rate above a minimum level and sustaining the elevated pulse rate for a minimum period of time. It would be a simple matter for one skilled in the art to provide a minimum exercise alarm which would alarm whenever the display pulse rate falls below a preset or a predetermined exercise pulse rate. A further feature would integrate the display pulse rate over time to provide a value indicative of total cardiovascular exercise conducted. In this case, an alarm could be activated after an elevated heart rate has been maintained for a predetermined period of time.

Finally, for patients suffering from cardiovascular disease, another embodiment of the claimed invention could be programmed to activate an alarm whenever the display pulse rate exceeds a predetermined value.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. An apparatus for noninvasive measurement of pulse rate comprising:
    a sensor, wherein said sensor senses at least one pressure or force and produces at least one sensor element signal indicative of said pressure or force;
    a gimbal device operably connected to said sensor, said gimbal device having at least one plate member and at least two axes perpendicular to each other and parallel to said at least one plate member, wherein said sensor is rotatable about said at least two axes by a predetermined angle;
    a spring element operatively connected at a first end to said gimbal device, said spring element pressing said sensor against a radial artery of a subject;
    a case, operatively connected to a second end of said spring element;
    a flexible printed circuit board operatively connected at a first end to said sensor;
    a central processing unit located in said case and operatively connected to a second end of said flexible printed circuit, said central processing unit determining a pulse rate based on said at least one sensor element signal received from said sensor;
    a display located in said case connected to said central processing unit, said display displaying said pulse rate; and playing said pulse rate; and
    a strap operatively connected to said case on at least two sides for holding said case on said subject, said strap at no time contacting said spring element.

2. The apparatus of claim 1, wherein said predetermined angle is about 20 degrees.

3. The apparatus of claim 1, wherein said sensor is a tonometer sensor having a plurality of pressure sensing elements disposed in an array for sensing a blood pressure on at least one of said pressure sensing elements and producing a plurality of sensor element signals, at least one of said sensor element signals being indicative of said blood pressure.

4. The apparatus of claim 1, wherein said strap further comprises:
    a first side having a first end operatively connected to said case;
    a protective band having a first end operatively connected to said case;
    a buckle operatively connected to a second end of said protective band, said buckle being operable to grip a second end of said first side to hold said case on said subject.

5. The apparatus of claim 4, wherein said protective band further comprises:
    a first and a second mounting pad located at said first and second ends of said protective band, respectively;
    a first and a second edge operatively connected to said first and second mounting pads, said first and second edges being disposed on opposite sides of said spring element while said case is held on said subject by said strap.

6. The apparatus of claim 1, wherein said spring element further comprises:
    a sensor position adjustment element operatively connected between said gimbal element and said first end of said spring element, and means for slidably mounting said gimbal element with respect to said sensor position adjustment element.

7. An apparatus for noninvasive measurement of pulse rate comprising:

a sensor wherein said sensor senses at least one pressure and produces at least one sensor element signal indicative of said pressure;

a case;

a spring element coupled at a first end to said sensor and at a second end to said case, said spring element pressing said sensor against a subject near a radial artery;

a flexible printed circuit board having a plurality of conductors operatively connected at a first end to said sensor;

a central processing unit located in said case and operatively connected to a second end of said flexible printed circuit board, said central processing unit determining a pulse rate based on said at least one sensor element signal received from said sensor;

a display located in said case and operatively connected to said central processing unit, said display displaying said pulse rate; and a strap operatively connected to said case on at least two sides for holding said case on a subject.

8. The apparatus of claim 7, wherein said spring element includes:

a gimbal device operably connected to said sensor, said gimbal device having at least one plate member and at least two axes perpendicular to each other and parallel to said at least one plate member, wherein said sensor is rotatable about said at least two axes by a predetermined angle; and a spring operatively connected at a first end to said gimbal device and at a second end to said case, said spring pressing said sensor against said subject near a radial artery.

9. The apparatus of claim 8, wherein said predetermined angle is about 20 degrees.

10. The apparatus of claim 8, wherein said spring element further comprises:

a sensor position adjustment element operatively connected between said gimbal element and said first end of said spring element, and means for slidably mounting said gimbal element with respect to said sensor position adjustment element.

11. The apparatus of claim 8, wherein said spring has predetermined radius of curvature.

12. The apparatus of claim 7, wherein said sensor is a tonometer sensor having a plurality of pressure sensing elements disposed in an array for sensing a blood pressure on at least one of said pressure sensing elements and producing a plurality of sensor element signals, at least one of said sensor element signals being indicative of said blood pressure.

13. The apparatus of claim 7, wherein said strap further comprises:

a first side having a first end operatively connected to said case;

a protective band having a first end operatively connected to said case;

a buckle operatively connected to a second end of said protective band, said buckle being operable to grip a second end of said first side to hold said case on said subject.

14. The apparatus of claim 13, wherein said protective band further comprises:

a first and a second mounting pad located at said first and second ends of said protective band, respectively;

a first and a second edge operatively connected to said first and second mounting pads, said first and second edges being disposed on opposite sides of said spring element while said case is held on said subject by said strap.

15. An apparatus for noninvasive measurement of pulse rate comprising:

a sensor wherein said sensor senses at least one pressure or force and produces at least one sensor element signal indicative of said pressure or force;

a gimbal device operably connected to said sensor, said gimbal device having at least one plate member and at least two axes perpendicular to each other and parallel to said at least one plate member, wherein said sensor is rotatable about said at least two axes by a predetermined angle;

a spring element operatively connected at a first end to said gimbal device, said spring element pressing said sensor against a subject near a radial artery;

a case, operatively connected to a second end of said spring element;

a central processing unit located in said case and operatively connected to said sensor, said central processing unit determining a pulse rate based on said at least one sensor element signal received from said sensor;

a display located in said case and operatively connected to said central processing unit, said display displaying said pulse rate; and a strap operatively connected to said case on at least two sides for holding said case on said subject, said strap at no time contacting said spring element.

16. The apparatus of claim 15, further comprising:

a flexible printed circuit operatively connected at a first end to said sensor and at a second end to said central processing unit and having at least one conducting path for conducting said at least one sensor element signal to said central processing unit.

17. The apparatus of claim 15, wherein said predetermined angle is about 20 degrees.

18. The apparatus of claim 15, wherein said sensor is a tonometer sensor having a plurality of pressure sensing elements disposed in an array for sensing a blood pressure on at least one of said pressure sensing elements and producing a plurality of sensor element signals, at least one of said sensor element signals being indicative of said blood pressure.

19. The apparatus of claim 15, wherein said strap further comprises:

a first side having a first end operatively connected to said case;

a protective band having a first end operatively connected to said case;

a buckle operatively connected to a second end of said protective band, said buckle being operable to grip a second end of said first side to hold said case on said subject.

20. The apparatus of claim 19, wherein said protective band further comprises:

a first and a second mounting pad located at said first and second ends of said protective band, respectively;

a first and a second edge operatively connected to said first and second mounting pads, said first and second edges being disposed on opposite sides of said spring element while said case is held on said subject by said strap.

21. The apparatus of claim 15, wherein said spring element further comprises:
   a sensor position adjustment element operatively connected between said gimbal element and said first end of said spring element, and means for slidably mounting said gimbal element with respect to said sensor position adjustment element.

22. An apparatus for noninvasive measurement of pulse rate comprising:
   a sensor means for sensing at least one pressure or force and producing at least one sensor element signal indicative of said pressure or force;
   means for pivoting said sensor means about an axis;
   means for pressing said sensor means against a subject near a radial artery;
   means for anchoring said pressing means;
   central processing means for determining a pulse rate based on said at least one sensor element signal received from said sensor means;
   means for displaying said pulse rate; and
   means for holding said anchoring means on said subject, said holding means at no time contacting said pressing means.

23. The apparatus of claim 22, wherein said pivoting means allows said sensor to pivot through a predetermined angle of about 20 degrees.

24. The apparatus of claim 22, wherein said sensor means is a tonometer sensor means having a plurality of pressure sensing elements disposed in an array for sensing a blood pressure on at least one of said pressure sensing elements and for producing a plurality of sensor element signals, at least one of said sensor element signals being indicative of said blood pressure.

25. The apparatus of claim 22, wherein said holding means further comprises means for protecting said sensor means and said pressing means.

26. The apparatus of claim 22, wherein said pressing means further comprises means for operatively connecting said pivoting means and said pressing means, wherein said connecting means adjusts at least one characteristic of said pressing means.

27. The apparatus of claim 22, wherein said central processing means further comprises:
   means for determining a plurality of average pulse rates based on said sensor element signal;
   means for computing a value corresponding to an autocorrelation of said sensor element signal over a predetermined time period; and
   means for calculating a display pulse rate based on at least two of said average pulse rates, each of said at least two pulse rates having a corresponding said value within a predetermined range.

28. The apparatus of claim 22, wherein said central processing means further comprises:
   means for calculating a plurality of slopes based on said sensor element signal;
   means for determining a plurality of average pulse rates based on said sensor element signal having corresponding said slopes greater than a predetermined slope threshold;
   means for computing a value corresponding to an autocorrelation of said sensor element signals over a predetermined time period; and
   means for calculating a display pulse rate based on at least two of said average pulse rates, each of said at least two pulse rates having a corresponding said value within a predetermined range.

29. An apparatus for noninvasive measurement of pulse rate comprising:
   a tonometer sensor means having a plurality of pressure sensing elements disposed in an array, for sensing blood pressure on at least one of said pressure sensing elements and producing a plurality of sensor element signals, at least one of said sensor element signals being indicative of said blood pressure;
   means for correcting said sensor element signals using a correction factor based on at least one characteristic of said sensor element signals;
   means for determining a plurality of average pulse rates based on said corrected sensor element signals;
   means for computing a value corresponding to an autocorrelation of said corrected sensor element signals over a predetermined time period;
   means for calculating a display pulse rate based on at least two of said average pulse rates, each of said at least two pulse rates having a corresponding said value within a predetermined range; and
   means for generating an output signal corresponding to said calculated display pulse rate.

30. An apparatus for noninvasive measurement of a cardiopulmonary parameter comprising:
   means for sensing a physiological parameter response to blood pressure;
   means for producing at least one sensor element signal indicative of said physiological parameter;
   means for determining a plurality of average cardiopulmonary parameters based on said at least one sensor element signal;
   means for determining a plurality of valid average cardiopulmonary parameters;
   means for calculating a display cardiopulmonary parameter based on at least two of said valid average cardiopulmonary parameters; and
   means for generating an output signal corresponding to said display cardiopulmonary parameter.

31. The apparatus of claim 30, wherein said means for sensing comprises a tonometer sensor means.

32. The apparatus of claim 30, wherein said means for determining further comprises:
   means for computing a value corresponding to an autocorrelation of said at least one sensor element signal;
   means for identifying said cardiopulmonary parameters having a corresponding said value within a predetermined range.

33. An apparatus for noninvasive measurement of a cardiopulmonary parameter comprising:
   a sensor means for sensing at least one cardiopulmonary parameter responsive to blood pressure and producing at least one sensor element signal indicative of said blood pressure;
   means for pivoting said sensor means about an axis;
   means for pressing said sensor means against a radial artery of a subject;
   means for anchoring said pressing means;
   central processing means for determining a cardiopulmonary parameter based on said at least one sensor element signal received from said sensor means;
   means for displaying said cardiopulmonary parameter;

means for holding said anchoring means on said subject, said holding means at no time contacting said pressing means.

34. The apparatus of claim 33, wherein said pivoting means allows said sensor means to pivot through a predetermined angle of about 20 degrees.

35. The apparatus of claim 33, wherein said holding means further comprises means for protecting said sensor means and said pressing means.

36. The apparatus of claim 33, wherein said pressing means further comprises means for operatively connecting said pivoting means and said pressing means, wherein said connecting means adjusts at least one characteristic of said pressing means.

* * * * *